United States Patent [19]

Takai et al.

[11] Patent Number: 5,698,228

[45] Date of Patent: Dec. 16, 1997

[54] WOUND HEALING COMPOSITION USING SQUID CHITIN AND FISH SKIN COLLAGEN

[75] Inventors: Mitsuo Takai, Sapporo; Yuichi Shimizu, Tomakomai; Josuke Shimizu, Sapporo; Kunio Yamazaki, Ebetsu; Yoshiteru Kumabayashi, Sapporo; Hideki Shimizu, Sapporo; Kunishige Yamada, Sapporo, all of Japan

[73] Assignees: Hokkaido Government; Daido Hoxan Inc., both of Sapporo, Japan

[21] Appl. No.: 669,956

[22] Filed: Jun. 25, 1996

[30] Foreign Application Priority Data

Jun. 26, 1995 [JP] Japan .................... 7-182172

[51] Int. Cl.$^6$ .................... A61K 35/56; A61K 35/60
[52] U.S. Cl. .................... 424/549; 424/538; 424/572; 424/543; 424/574
[58] Field of Search .................... 424/538, 572, 424/543, 574, 549; 514/2.21, 55

[56] References Cited

U.S. PATENT DOCUMENTS 4,703,108  10/1987  Silver et al. .................... 530/356
4,958,012  9/1990  Tokura et al. .................... 536/20

*Primary Examiner*—Jean C. Witz
*Attorney, Agent, or Firm*—Jacobson, Price, Holman & Stern, PLLC

[57] ABSTRACT

There is provided a skin substitute that can suitably be used for covering the surface of a damaged skin area which is typically a wound produced by a traumatic local loss of the skin of the human body as a result of a burn or some other cause of damage. It is a skin substitute of a laminate comprising a squid chitin sheet and a fish skin collagen coat layer, which may be a salmon skin collagen coat layer. Such a skin substitute effectively exploits the suppleness and the effect of proving an environment for encouraging the production of lysozyme and defending the wound of squid chitin and, at the same time, compensate the disadvantage of poor adhesion of fibroblast cells that operate for curing the wound. Additionally, the fibroblast cells adhering to a laminate of a squid chitin sheet and a fish skin collagen coat layer showed a normal cell proliferation curve without any delayed initial rising phase to prove the former more satisfactory that cannot be expected from a laminate comprising a calf skin collagen coat layer. Finally, a DNA labeling index substantially equal to that of fibroblast cells of normal human skin was observed.

5 Claims, 4 Drawing Sheets

WOUND HEALING COMPOSITION USING SQUID CHITIN AND FISH SKIN COLLAGEN

BACKGROUND OF THE INVENTION

1. Field of the Invention

This invention relates to a skin substitute (wound-healing material) that can suitably be used for covering the surface of a damaged skin area which is typically a wound produced by a traumatic local loss of the skin of the human body as a result of a burn or some other cause of damage.

2. Prior Art

The skin comprises three layers of epidermis, dermis and hypodermis. When the dermis is totally damaged, if locally, as a result of a burn or for some other reason, it cannot be regenerated and keloid appears on the damaged area to replace the dermis. While skin graft is a sole method known to date for completely and perfectly restoring the skin of the damaged area, the only feasible source of skin that can be used for transplantation is the patient him- or herself and, if applicable, the other one of the monozygotic twins. A number of skin substitutes, or artificial skin, have been proposed to solve this problem. Some of them are put to practical applications while the others are still on the way of technological development.

Known artificial skins that have been put to practical use include semisynthetic film of various types prepared by resynthesizing tissues of organisms such as collagen film in the form of nonwoven tissues of collagen obtained by refining the skin of swine (marketed in 1982) or that of bovine, chitin film in the form of nonwoven tissues of chitin obtained from crab shell (marketed in 1988) and chitin in the form of sheets obtained from squid pen (a Loligo, refined and isolated squid chitin).

However, any of the artificial skins including collagen film obtained from the skin of swine or that of bovine and chitin film of crab do not provide a satisfactory suppleness nor a sufficient adhesion for fibroblast on the interface of the artificial skin and the surface of a wound. Nor do they encourage the proliferation of fibroblast.

While sheets of squid chitin, which are still on the way of of development, excel any other known comparable products in terms of suppleness, they are still not satisfactory from the viewpoint of adhesion and proliferation of fibroblasts.

SUMMARY OF THE INVENTION

In view of the above identified problems that are inevitable for any artificial skins of refined and isolated cells, it is, therefore, the object of the present invention to exploit the advantages of a sheet of squid chitin that is supple and promotes the production of lysozyme to protect the wound and, at the same time, resolve the disadvantages that fibroblast for healing the wound does not adhere to it satisfactorily and it does not particularly encourage the proliferation of cells by forming a laminate of a sheet of squid chitin and a layer of collagen of the fish skin obtained from salmon, trout, walleye pollack, flying fish and shark that has not been used for artificial skin. Such a laminate can improve the adhesion and proliferation of cells and prevent the transmutation of normal cells into cancer cells by transforming factors in the course of cell proliferation.

According to the invention, the above object is achieved by providing a skin substitute using marine organisms and comprising a sheet of squid chitin as a substrate and a laminar layer of fish skin collagen laid on the substrate.

DESCRIPTION OF THE PREFERRED MODE OF CARRYING OUT THE INVENTION

EXAMPLE

A skin substitute according to the invention is prepared by laminating a sheet of squid chitin and a layer of laminar collagen of fish skin by means of a known appropriate technique. For example, such a laminate can be prepared by casting a sheet of squid chitin, pouring collagen of fish skin and drying both the chitin and the collagen in a refrigerator for about a week.

Before describing the method of manufacturing a sheet of squid chitin for the purpose of the invention and a known method of manufacturing crab chitin for comparison, some of the major differences of the two different chitins will be pointed out. The chitin available from the squid pen is soft and called β-chitin, which has a different crystal structure from that of the chitin from crab shell, which is called α-chitin, although the amount of the chitin obtainable from a single is only about 1/40 of that of the chitin extractable from a single crab. It is easy to swell with water and can be formed into a sheet relatively with ease. It shows a higher permeability to water vapor and a higher hygroscopicity than the chitin of crab to make it more suitable for a skin substitute. The chitin shows an excellent digestibility in the living body and, as described above, encourages the production of lysozyme to provide a good environment for defending the living body.

Since the squid chitin has a soft crystalline structure, it can be easily disintegrated into water by a simple device such as a mixer and does not requires a complicated process of dissolving into a solvent, regeneration by formatting a sheet with a binder as in the case of crab chitin. Thus, the squid chitin provides an advantage of low energy cost.

In an example, a sheet of squid chitin was produced by a batch type suction paper-making machine.

1) A 3 g of refined squid chitin was dispersed in a 300 ml of distilled water and disintegrated into the water by a mixer twice, with 40V for 5 min. and 70V for 10 min.

2) The sheet making solution was poured into a large Buchner funnel of a batch type suction paper-making machine having a bottom area of 0.24 $m^2$ (a diameter of 17.5 cm) to produce three different weights of 10, 20 and 40 (g/$m^2$) and then subjected to a suction paper making process. Teflon-made filter paper was used for filtration in the process.

3) Each of the produced squid chitin sheets having different thicknesses was then sandwiched between five sheets of teflon filter paper and a teflon panel and pressed under a pressure of 3 kg/cm² for three (3) minutes and this press operation was repeated twice.

4) The filter paper sheets were replaced with new ones and the produced squid chitin sheet was air-dried while being pressed under three telephone books.

5) The filter paper sheets were replaced again with new ones after four hours and the squid chitin sheet was dried further for 20 hours to produce the final product of a squid chitin sheet.

On the other hand, a crab shell chitin sheet was prepared by a homogenizing technique, where the crab chitin was reduced to microfibril by mechanically applying high pressure because of a relatively hard crystalline structure. The use of high pressure for producing a crab chitin sheet was determined by taking the possibility into consideration that, when the chitin was dissolved into a solvent, the native microfibrillar structure of crab chitin can be destroyed to make the product heavily defective.

The technique used for the operation of producing a crab chitin sheet was as follows.

1) Distilled water was made to circulate in a 15MR-Laboratory Homogenizer available from Gaulin and the internal pressure was raised to 30,000 kg/cm² before refined crab chitin (20 mesh) was slowly poured into the apparatus and homogenized until no granular crab chitin was observed in the suspension of crab chitin, which was then used as the raw solution for the subsequent papermaking process.

2) Thereafter, the above described papermaking process for squid chitin was used also for crab chitin in the same batch type suction paper machine.

Table I below shows the thickness and the weight per unit area of each of the prepared sample sheets of squid chitin and crab chitin.

TABLE I

|  | Thickness (μm) | Weight per Unit Area (g/cm²) |
| --- | --- | --- |
| Squid Chitin Sheet (1) | 15 | 10.5 |
| Squid Chitin Sheet (2) | 27 | 21.9 |
| Squid Chitin Sheet (3) | 46 | 44.5 |
| Crab chitin | 35 | 21.9 |

Some of the results of analysis of the samples of squid chitin and crab chitin will be described in detail hereinafter.

Table II below shows the stiffness of each of the samples obtained as a result of a bursting strength test, a tensile strength test and a tearing resistance test and the dynamic Young's modulus of the sample.

TABLE II

|  | Weight per Unit (g/m²) | Breaking Length (km) | Bursting Strength kP-m²/g | Tearing Resistance kN-m²/g | Stiffness |
| --- | --- | --- | --- | --- | --- |
| Squid Chitin Sheet (1) | 21.9 | 6.9 | 6.9 | 37 | 12 |
| Crab Chitin Sheet | 21.9 | 7.9 | 3.8 | immeasurable | 66 |

As seen from the above table, while each of the squid chitin sheets showed a breaking length substantially equal to that of the crab chitin sheet, its bursting strength was twice as great as that of the crab chitin counterpart and its tearing resistance was more than $10^2$ times greater than that of the crab chitin sheet. (The tearing resistance of the crab chitin sheet was a fraction of a unit and hence is not shown in Table II.) On the other hand, it showed a suppleness more than five (5) times greater than the crab chitin sheet. The difference may be based on the structural difference between the fibril structure and the lamella structure that chitin may take and also on the above described fact that the crab chitin is α-chitin whereas the squid chitin is β-chitin which is different from α-chitin in terms of crystal structure.

While the squid chitin has a tearing resistance and a bursting strength considerably greater than those of the crab chitin, the former is five times more supple than the latter as shown in Table II. These properties on the part of squid chitin makes it very suited for the wound if it is used as a skin substitute. Additionally, the squid chitin is more advantageous over the crab chitin because, unlike a sheet of crab chitin, no paper making process is required to produce a sheet of squid chitin.

Now, the fish skin collagen, the other component of a skin substitute according to the invention, will be described in terms of the manufacturing process thereof.

The marine products processing industry produces at an enormous rate industrial wastes such as skin, bones, heads and internal organs of processed fish. In view of the fact that marine products are used solely as foods at present, it will be a major breakthrough if any of these wastes can be used as resources for producing new products. The collagen contained in the skin of salmon, trout and other fish attracts attention from this point of view.

As is already known, a collagen molecule comprises peptide chains having no helical structure at the opposite terminals, which are called telopeptide. Telopeptide contains 12 to 27 amino acid residues and it is believed that the antigenicity of collagen is activated by these chains. Therefore, the telopeptide of collagen has to be eliminated before collagen is used for living organisms and a method for eliminating the telopeptide is treating it with pepsin.

Now, the technique used for producing collagen of salmon skin for the purpose of the invention will be described below.

1) Defatted salmon skin was put into a 0.2M acetic acid solution to a ratio of 1:15 (w:v) and the mixture was stirred lightly and left at 4° C. for three (3) days.

2) The salmon skin/acetic acid solution was diluted by another 0.2M acetic acid solution and subjected to a centrifugal process with 30,000 g at 5° C. for 30 minutes.

3) Pepsin was added to the supernatant by 1 wt % relative to the substrate in order to treat the latter with pepsin for 24 hours.

4) The treated solution was put into a dialyzing diaphragm and subjected a salting-out process by using 10% sodium chloride for 48 hours and the reaction product was subjected to a centrifugal process with 30,000 g at 5° C. for 30 minutes.

5) The supernatant was removed and the collagen residue was dissolved into a 0.2M acetic acid solution at 4° C. for two (2) days.

6) The solution of 5) was put into a dialyzing diaphragm and the steps 3) through 5) were repeated three (3) times.

7) The refined collagen solution was put into a dialyzing diaphragm again and dialyzed into distilled water.

8) The perfectly neutralized collagen solution was freeze-dried to prepare a dried sample.

The property of the obtained salmon skin collagen that seemed most important to the present invention may be that its thermal denaturation temperature is considerably lower than that of bovine skin collagen.

Figure 1:
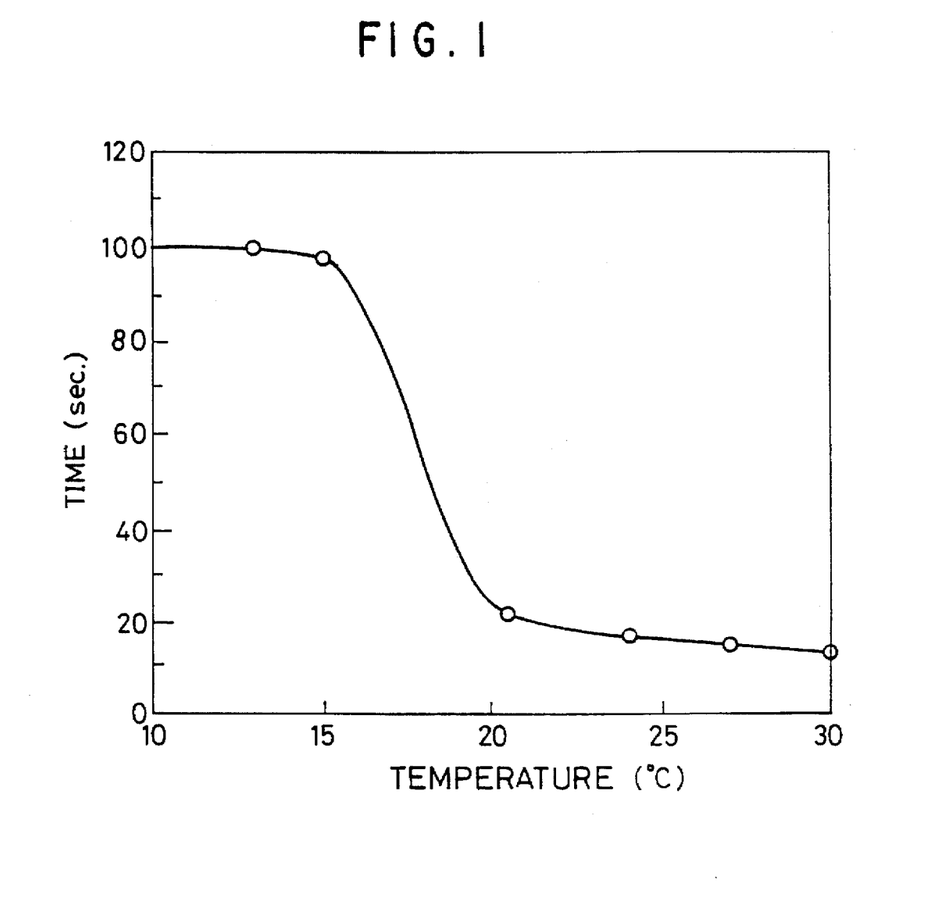
FIG. 1 shows the relationship between the viscosity and the temperature of a laminar collagen of salmon skin that can be used for a skin substitute according to the invention, as obtained in an experiment.

More specifically, collagen has a triple helical structure of three polypeptide chains with molecular weight of about 100,000 and the structure is stabilized by the hydrogen bonds binding the polypeptide chains. As it is heated, the hydrogen bonds are broken to produce gelatin having a random coil structure. At this time, the collagen greatly changes its physical properties including the viscosity of solution and the optical rotation as a result of thermal denaturation. The temperature at which such thermal denaturation occurs is one of the essential properties of collagen. The specimen of salmon skin collagen obtained by the above described technique was disintegrated into an acetic acid buffer solution of pH 5.0 to a concentration of 0.5% and the temperature of the solution was raised from 4° C., observing the viscosity by means of an Ostwald viscometer to determine the thermal denaturation temperature. FIG. 1 shows the obtained result for the relationship between the temperature and the viscosity. As shown in FIG. 1, the viscosity drops dramatically at temperature between 15° to 20° C.

In other words, the thermal denaturation temperature of salmon skin collagen is about 16° to 18° C., which is remarkably lower than the comparable temperature of bovine skin collagen or about 37° to 38° C. It is known that the denaturation temperature of collagen is closely related to the organism it originates from and the above fact may be explained by that salmon is a fish living in the cold tidal current.

As for the salmon skin collagen, its hydroxyproline content is only two-thirds (⅔) that of calf skin collagen (denaturation temperature: 37° C.). Since hydroxyproline participates the intramolecular hydrogen bond, the low hydroxyproline content may provide one of the causes of the low denaturation temperature of salmon skin collagen.

The solution of salmon skin collagen is gelled quickly at temperature below 4° C. and pH 7.5 and the melting point of the produced gel is about 3.6° C. On the other hand, the calf skin collagen is not gelled until the temperature rises to 37° C. As described above, this fact may be explained by the fact that salmon is a fish living in the cold tidal current and the salmon skin collagen forms stable collagen tissue at about 15° C. Thus, the hydroxyproline content is also related to the gel point of collagen. A skin substitute according to the invention and comprising a squid chitin sheet and a layer of fish skin collagen is used by directly applying the squid chitin sheet to the surface of a wound. Therefore, the squid chitin is required to encourage the proliferation of the fibroblast comprised in the dermis in order to heal the wound. The process of proliferation of cells starts as the cells adheres to the tissue and/or the matrix. Thus, a large number of cells have to be caused to adhere to the tissue and/or the matrix for proliferation. On the other hand, cells should not be transformed into cancer cells before they proliferate. Taking these matters into consideration, the number of cells, the number of proliferated cells and the DNA labeling index of cells were observed on a skin substitute sample as will be described hereinafter.

Fibroblast cells were subjected to an operation of passage culture. More specifically, as cells multiplies to completely cover the wall of the culture vessel with a layer of cells or the culture vessel is overpopulated with cells, the overpopulation has to be dissolved by transferring some of the cells into another culture vessel to form a subculture and this transfer operation is referred to as passage culture. For passage culture, an even suspension of cells is prepared by taking the cells from the original culture vessel and, after counting the number of the cells, the suspension is diluted to an appropriate concentration and moved into a new culture vessel.

For the purpose of the invention, fibroblast cells were cultured in the following manner.

1) The medium of a flask (with a bottom of 75 cm$^2$) containing fibroblast cells was sucked by means of a Pasteur pipette.

2) The inner bottom surface of the flask was washed with a 15 ml of Hanks' BSS w/o $Ca^{2+}Mg^{2+}$ three (3) times.

3) A 10 ml of 0.05% Trypsin EDTA (0.5% Trypsin 53 mM EDTA-4Na 11 m+Hanks' BSS 9 ml) was put into culture flask, incubated for five (5) min. and the fibroblast cells ware separated from the bottom of the culture vessel.

4) The suspension of cells was pipetted 10 times and a 1 ml of FCS was added thereto as single cells and the mixture was centrifuged at a rate of 1,000 to 1,500 rpm for five (5) minutes.

5) The supernatant was sucked by means of a Pasteur pipette and put into a 12 ml of culture medium solution. A 100 µl of the medium carrying cells therein was taken and diluted to 20 ml by Isoton II.

6) The number of the cells found with a diameter of 10 to 30 µm in a 500 µl of the diluted solution was counted by means of a Coulter counter. Part of the remaining suspension of fibroblast cells was used to transplant fibroblast cells into a culture flask so that the 75 cm$^2$ bottom of the flask was populated at a rate of 104 cells/cm$^2$. Then, the flask was filled with a 20 to 30 ml of culture medium solution.

7) The flask was put into a $CO_2$ incubator controlled to 37.0° C. and $CO_2$ 5%.

As described above, the materials of the skin substitute used on a wound exert a great influence on the cure of the wound because the skin substitute is directly held in contact with the surface of the wound in the regeneration process of the skin of the patient. Particularly, the proliferation of fibroblast is a major booster for the regeneration of dermis. If the dermis is totally destroyed, if locally, it cannot be regenerated and keloid appears on the damaged area to replace the dermis.

In the process of proliferation of fibroblast, each fibroblast cell adheres to the matrix and expands to a starlike form, which is characteristic to the fibroblast, and then contracts as it is separated from the matrix at an end before it is divided into two, which then adhere to the matrix. Thus, in order for a wound covering material to encourage the fibroblast to proliferate, fibroblast cells have to adhere properly to the wound covering material. In an experiment, the number of the cultured fibroblast cells (passage between 4th and 8th) adhering to a skin substitute (wound covering material) was counted by means of a Coulter counter.

Three skin substitutes comprising squid chitin sheets with respective weights per unit area of 10, 20 and 40 g/cm$^2$ and a coat layer of fish skin collagen were prepared as specimens for the above experiment. Additionally, an atelocollagen film was used for comparison. (See Table III.) The number of the fibroblast cells on the chitin sheet of each of the specimen was counted at regular intervals (Attachment). The experiment will be described below.

1) After the above described operation of passage culture, the culture medium was replaced every three days for each of the specimens and the fibroblast cells cultured for 10 to 14 days were separated from the culture medium by means of trypsin and collected by means of a centrifuge.

2) A cell suspension was prepared for each of the specimens by stirring collected pellets in a culture medium.

3) The cells in the suspension was counted by means of a Coulter counter and fibroblast cells were added until the cell concentration got to 50,000 cells/cm$^2$.

4) A 2 ml of the liquid culture was then left in an environment of 5% $CO_2$ and 37° C. for 3, 6, 24 and 48 hours for observation.

5) After completing the culture operation, each of the specimens was washed three (3) times and the cells were separated by a 2 ml of Trypsin EDTA.

6) The cells with a diameter of 10 to 30 μm were counted by means of a Coulter counter.

Figure 2:
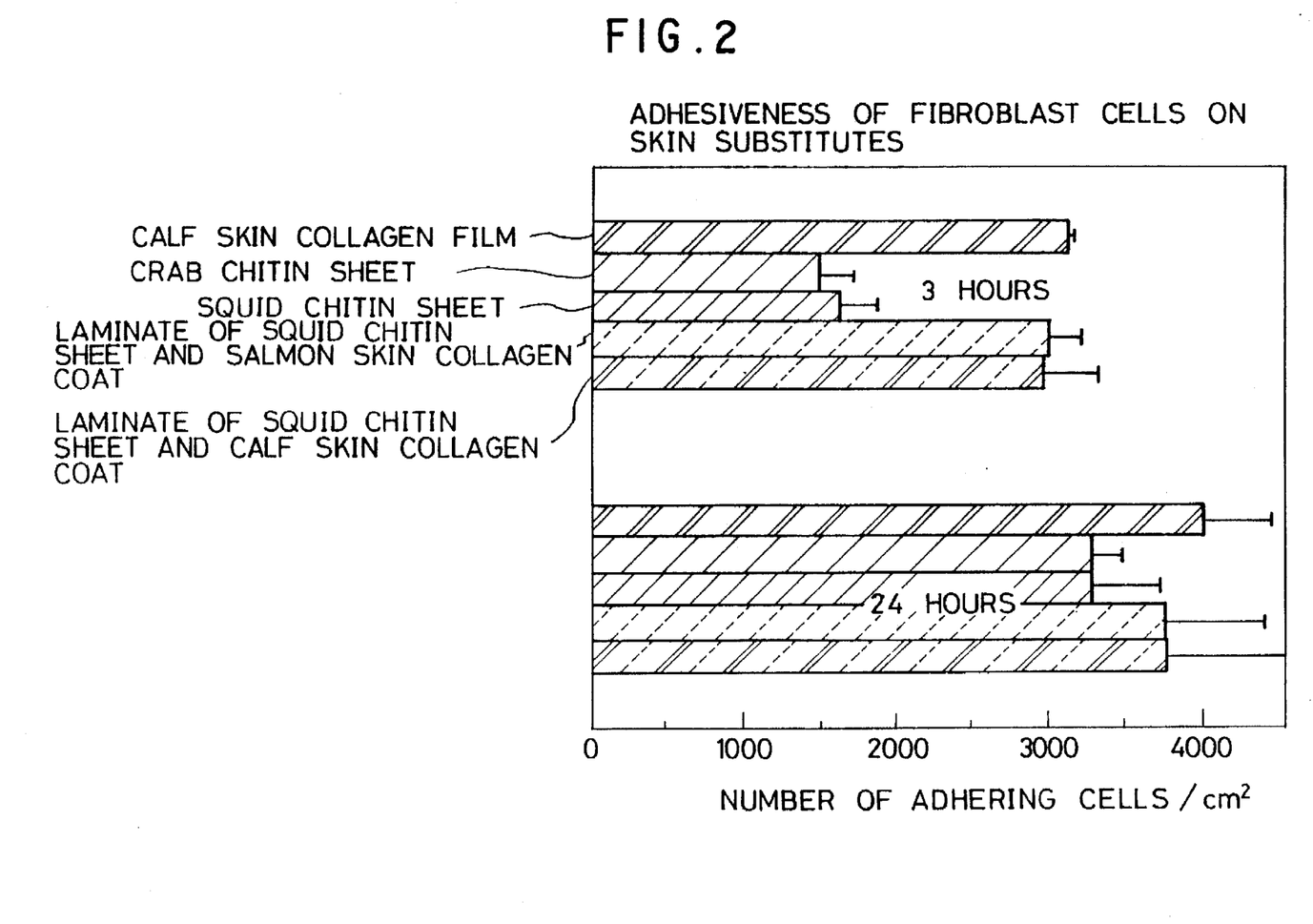
FIG. 2 shows the change with time of the number of fibroblast cells adhered to a skin substitute according to the invention.

FIG. 2 shows the number of fibroblast cells counted three (3) hours and 24 hours after the start of culturing for each of the chitin sheet specimens. When counted three (3) hours after the start, half of those adhering to a collagen film for culturing tissue cells for any of the chitin sheet materials but a laminate of a squid chitin sheet and a salmon skin collagen coat showed a number of cells adhering thereto that equaled to 90% of the cells on the collagen film. When counted 24 hours after the start, the ratio of the cells on the chitin sheet to those on the collagen film was only 80% for any of the chitin sheet materials to prove that a chitin sheet can poorly hold fibroblast cells. In order for a wound to encourage the skin to be regenerated there, there needs a substrate on which fibroblast cells proliferate and, if a skin substitute is used, it has to take the role of such a substrate. A squid chitin sheet can dramatically increase the number of fibroblast cells adhering thereto if it is coated with salmon skin collagen or calf skin collagen.

A fibroblast cell expands to a starlike form in the course of proliferation. More specifically, the proliferation starts after the expansion to a starlike form. Since the proliferation of cells significantly depends on how they adhere to a substrate, the specimens were observed through an optical microscope to see the mode of adhesion of cells. For this observation, fibroblast cells were cultured on a chitin sheet as in the case of the Attachment. Thereafter, the following operation was carried out.

1) The chitin sheet was taken out of the culture medium with fibroblast cells adhering thereto and washed with PBS.

2) The fibroblast cells on the washed chitin sheet were fixed for one (1) hour with 70% EtOH.

3) The ethanol was completely removed and the specimen dyed with hematoxylin.

4) The specimen was observed to see how cells were adhering to the chitin sheet.

As a result of the observation using an optical microscope, it was found that the starlike expansion of fibroblast cells was poorly observable on the chitin sheet using only squid chitin and the cells were globular as if they were in solution. On the other hand, the starlike expansion of fibroblast cells was clearly observable on the chitin sheet carrying a coat of fish skin collagen or calf skin collagen. If viewed with the result of the observation on the number of cells adhering to each of the specimens described above, it would be clear that collagen operates more effectively as a cell carrier than squid chitin. Although it is believed that chitin is antibacterial and hence effective for curing wounds, it is not particularly advantageous for causing adhesion of cells but the disadvantage can be remedied by using it with a collagen coat layer.

The chitin produces lysozyme to provide an environment good for the protection of living organisms but does not particularly encourage the proliferation of fibroblast cells. On the other hand, the collagen actively adheres cells if the collagen molecules shows a fibril structure (to produce fibrils), it is said that it can suppress the proliferation of cells. It has been reported that a solution of calf skin collagen or human placenta collagen produce fibroblast cells in a physiologically active environment and is gelled. The collagen should meet the requirement of taking the role of structurally maintaining living organisms as protein in a physiologically active environment. In view of this property on the part of collagen, it is quite probable that the collagen originating from a foreign creature does not produce filbrils in the human body in a physiologically active environment nor suppress the proliferation of cells. Thus, specimens of a laminate of a squid chitin sheet and a salmon skin collagen coat were prepared and the cell proleferation pattern was observed on the specimens along with other skin substitute specimens.

In this experiment, fibroblast cells of the 4th through 8th passage cultures were used and the proliferated cells were counted on each of the tested skin substitutes (wound covering materials) by means of a Coulter counter.

Cells are made to adhere to the specimens at a rate of 5,000 cells/cm$^2$ and the multiplied cells (growth) were counted. The growth on each of the squid chitin base sheets having different thicknesses was observed for comparison. As a control, a collagen film for culturing epidermal cells was used. Coat layers of different types of collagen were used for comparison. Base layers of chitin originating from different sources were also used for comparison.

The experiment was conducted in the following manner.

1) After an operation of passage culture, the culture medium was replaced every three days for each of the specimens and the fibroblast cells cultured for 10 to 14 days were separated from the culture medium by means of trypsin and collected by means of a centrifuge.

2) A cell suspension was prepared for each of the specimens by stirring the collected pellets in a culture medium.

3) The cells in the suspension was counted by means of a Coulter counter and fibroblast cells were added until the cell concentration got to 5,000 cells/cm$^2$.

4) A 2 ml of the liquid culture was then left in an environment of 5% $CO_2$ and 37° C. for 2, 4, 6 and 8 days for observation.

5) After completing the culture operation, each of the specimens was washed three times and the cells were separated by a 2 ml of Trypsin EDTA.

6) The cells with a diameter of 10 to 30 μm were counted by means of a Coulter counter.

Figure 3:
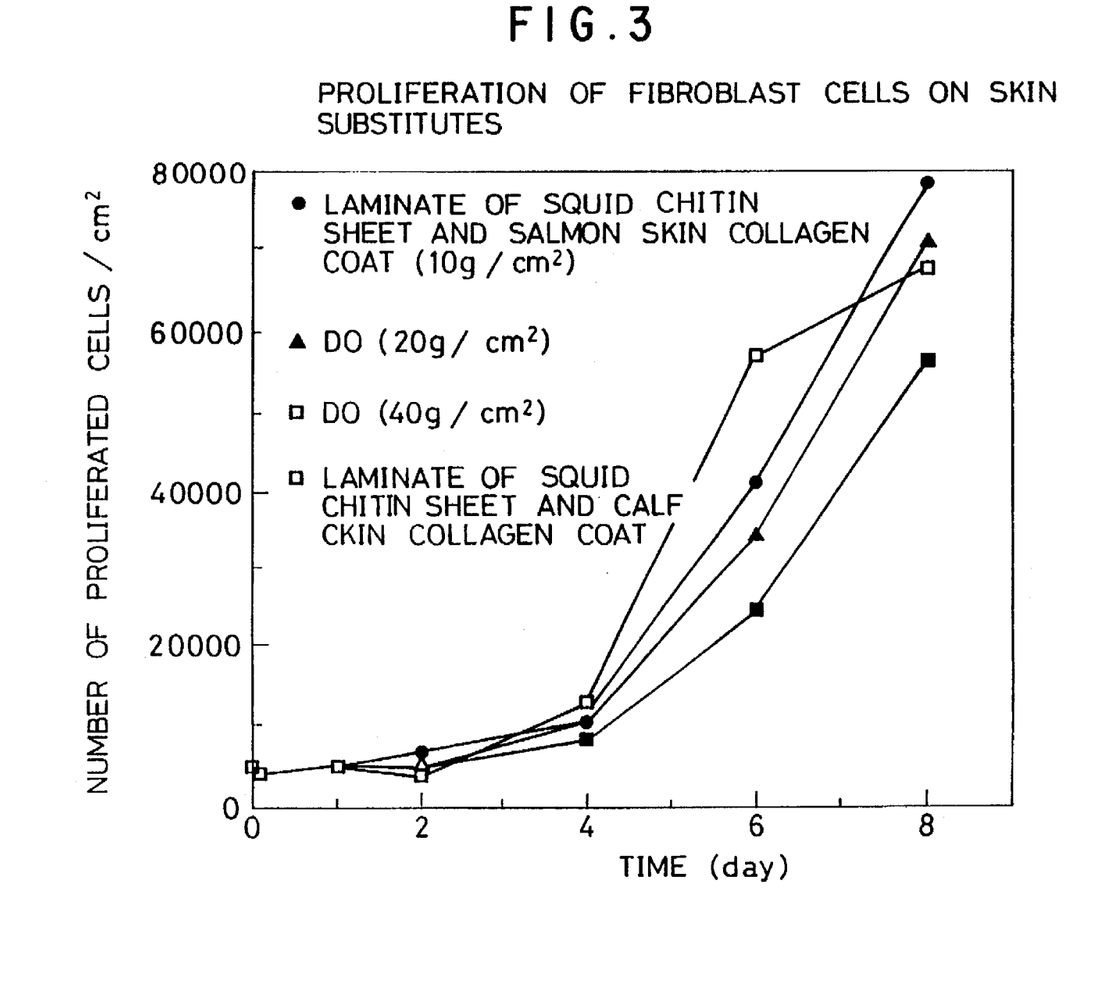
FIG. 3 shows the relationship between the number of proliferated fibroblast cells and the elapsed time for a number of different skin substitutes according to the invention and having different thicknesses of the laminar collagen layer of salmon skin.

FIG. 3 illustrates the result of the experiment.

Figure 4:
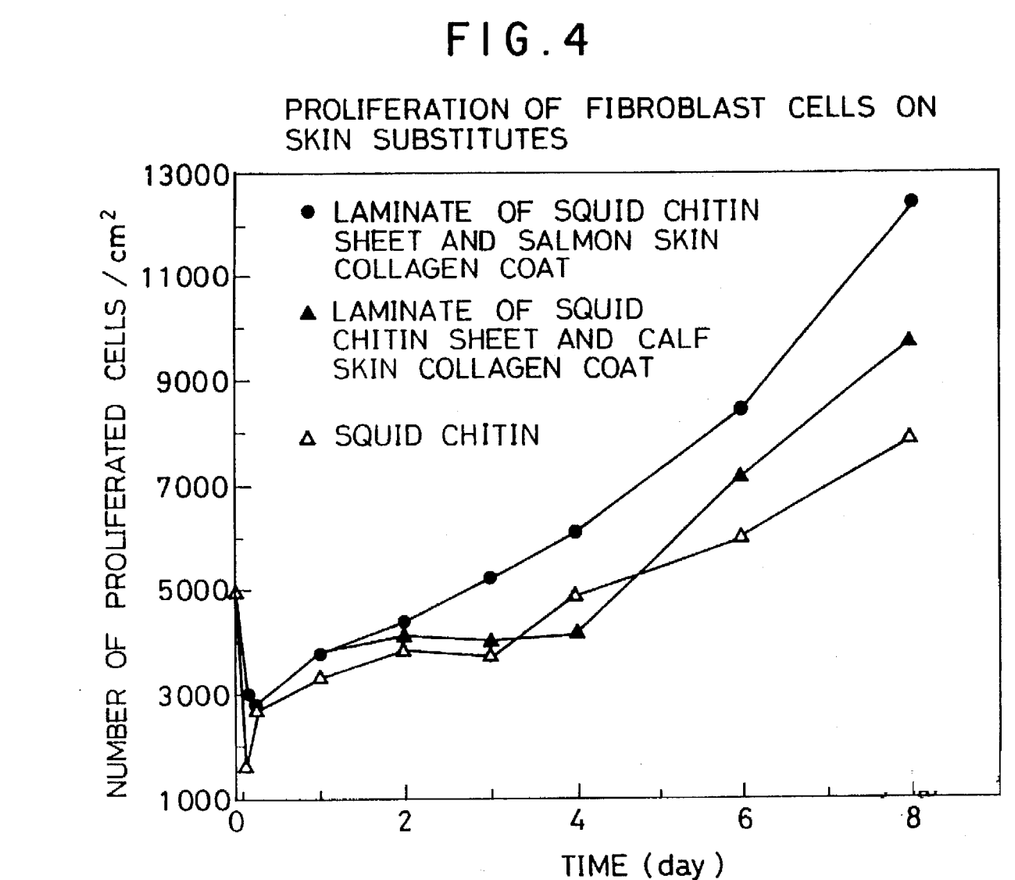
FIG. 4 shows the relationship between the number of proliferated fibroblast cells and the elapsed time for a skin substitute according to the invention, a skin substitute comprising a squid chitin sheet and a layer of calf skin collagen, a skin substitute comprising only a squid chitin sheet.

The specimen comprising a squid chitin sheet and a salmon skin collagen coat layer and the one comprising a squid chitin sheet and a calf skin collagen coat layer showed a substantially same and normalcell proliferation pattern. The thickness of the chitin sheet did not show any relationship with the proliferation activity of cells. As shown in FIG. 4, the proliferation was boosted by using a coat layer of salmon skin or calf skin on a squid chitin sheet. While the cell proliferation on a laminate comprising a salmon skin collagen coat layer showed an ideal pattern, the one on a laminate comprising a calf skin collagen coat layer showed a delayed initial rising phase. The salmon skin collagen returns to an amorphous state at 37° C. in a physiologically active environment, the calf skin collagen remains in a fibrous state under the same conditions. Since fibrous collagen operates to suppress the proliferation of cells, the coat layer of the calf skin collagen in a fibrous state must have delayed the initial rise phase of cell proliferation. Thus, a skin substitute comprising a salmon skin collagen layer is more effective than its counterpart comprising a calf skin collagen layer.

However, it should be noted that cells do not necessarily proliferate normally at all times. Particularly when cells proliferate at a high rate, the DNAs in some of the cells may be damaged in some way or other to transform those cells into cancer cells. Therefore, the cells on each of the skin substitute specimens were checked for transformation that might be attributable to the chitin sheet and/or the collagen of the specimen. DNAs were synthesized in vitro in a culture medium containing 5-bromo-2-dioxyuridine (BrdU) by means of an immuno-histo-chemical technique to visualize the cells after the S-stage (DNA synthesizing stage) and the DNA labeling indexes were observed.

The techniques used for the above observation will be described below.

Cell Culture

1) Fibroblast cells taken from the human dermis were planted on the 75 cm$^2$ large bottom of a flask at a rate of 104 cells/cm$^2$ and cultured for two (2) weeks. Thereafter, they were washed with 15 ml of Hanks' BSS w/o Ca$^{2+}$+Mg$^{2+}$ three times.

2) The cells were separated by means of Trypsin EDTA (0.005%) and collected by means of a centrifuge. The collected cells were suspended in an MEM with 10% FCS and 1% PC-ST and planted on each of the specimens to a concentration of 50,000 cells/cm$^2$.

3) The cells were then cultured for 24 hours in a 5% $CO_2$ environment.

BrdU Labeling

4) A 5 mm square piece was cut from each of the specimens and a 10% thermally immobile fetal calf serum was added thereto. The mixture was then put into a vial containing nucleoside-and-nucletide-free α-MEM, to which 100 µM BrdU was added.

5) The environment was replaced by a mixture of 95% $O_2$ and 5% $CO_2$ and, thereafter, the vial was closed by means of a teflon rubber cap. The internal pressure was raised to three (3) arms and the cells were incubated for one (1) hour at 37° C. in a shaking water bath.

Immuno-histo-chemistry

1) After washing each of the labeled tissues with PBS for 10 minutes, the cells were separated from the underlying layer by means of Trypsin EDTA (0.005%) and centrifuged for five (5) minutes at a rate of 1,500 rpm. The collected pellets were then scattered on a slide glass.

2) The tissue was then incubated in 2N HCl at room temperature for 40 minutes to denature the DNAs.

3) The incubated tissue was then washed with pH 9 PBS and pH 7.4 PBS and diluted with an anti-BrdU monoclonal antibody (anti-BrdU) (=mouse IgG) to a ratio of 1:100. Thereafter, it was incubated in a moist chamber at room temperature.

4) The tissue was washed with PBS for 30 minutes.

5) The tissue was then incubated by means of a biotin marking rabbit anti-mouse IgG antibody for 20 minutes.

6) The tissue was washed with PBS for 30 minutes.

7) The tissue was then incubated by means of peroxydase marking streptoavidin.

8) The tissue was washed with PBS for 30 minutes.

9) The antibody binding section of the tissue was visualized by means of diaminobenzidine. (50 ml PBS/50 ml distilled water/33 µl $H_2O_2$/3 mg diaminobenzidine for 10 minutes.)

In the DNA synthesis in vitro, part of the skin cells were cultured in a culture medium containing bromodioxyuridine (5-bromo-2"-deoxyuridine) to be more accurate (which makes nucleic acid functionally inoperative by surrounding it with a DNA synthesis inhibitor. In a living organism, it is taken into DNA as a substance resembling thymidine and induces a mutation because it gives rise to mispairing with guanosine.) and, thereafter, the nucleus of each cell is labeled after the S-stage. A malignant disease tends to raise the DNA labeling index.

In a recent report, the synthesizing velocities of tumor cells cultured on different media in vitro under high pressure in an environment of 95% $O_2$ and 5% $CO_2$ were compared. Table III below shows the result of an experiment carried out in a manner as described above in vitro under high pressure, where the technique of BrdU labeling was used.

TABLE III

DNA Labeling Index of Human Skin Cells

| Sample (Number of Samples) | Labeling Index |
| --- | --- |
| Calf Skin Collagen Film (3) | 1.3 ± 0.4% |
| Squid Chitin Sheet (3) | 1.0 ± 0.1% |
| Laminate of Squid Chitin/ Salmon Skin Collagen (4) | 1.7 ± 0.5% |
| Laminate of Squid Chitin/ Calf Skin Collagen (3) | 1.5 ± 0.5% |
| Normal Skin Cells (4) | 1.4 ± 0.4% |
| Bowen's Disease Cells (10) | 7.7 ± 1.4% |
| Ordinary Cancer Cells (5) | 8.5 ± 1.2% |

As seen from Table III above, the labeling indexes on the squid chitin sheet, salmon skin collagen coated squid chitin sheet and calf skin collagen coated squid chitin sheet were substantially equal to that of fibroblast cells of ordinary human skin within an allowance +−15%. On the other hand, the Bowen's disease cells and the Basal Cell Carcinoma showed respective DNA labeling indexes that are more than five (5) times greater than that of the normal skin cells. Thus, there was no indication that the proliferation of fibroblast cells on each of the skin substitute specimens was boosted by transformation into cancer cells.

Advantages of the Invention

As described above in detail, according to the invention, there is provided a laminate of a squid chitin sheet and a fish skin collagen coat layer to effectively exploit the suppleness and the effect of providing an environment for encouraging the production of lysozyme and defending the wound of squid chitin and, at the same time, compensate the disadvantage of poor adhesion of fibroblast cells that operate for curing the wound and that of not causing the fibroblast cells adhering thereto to expand to show a starlike form. Additionally, while the fibroblast cells adhering to a laminate of a squid chitin sheet and a fishskin collagen coat layer showed a normal cell proliferation curve, those adhering to a laminate of a squid chitin sheet and a calf skin collagen coat layer showed a delayed initial rising phase to prove the former more satisfactory. This is because the salmon skin collagen is amorphous in a physiologically active state, whereas the calf skin collagen produces collagen tissue and suppress the proliferation of fibroblast cells as confirmed by an experiment using various collagen coat layers arranged on a Petri dish. Therefore, it can be safely concluded that a laminate of a squid chitin sheet and a fish skin collagen coat layer is highly effective as a skin substitute. Finally, by observing the DNA labeling indexes of various samples, it was found that a squid chitin sheet, a laminate of a squid chitin sheet and a fish skin collagen coat layer, a laminate of a squid chitin sheet and a calf skin collagen coat layer and the normal human skin showed a substantially same value for DNA labeling index. Thus, again, it can also be safely concluded that a laminate of a squid chitin sheet and a fish skin collagen coat layer is highly effective as a skin substitute.

What is claimed is:

1. A wound healing composition comprising a sheet of squid chitin laminated to a layer of fish skin collagen wherein the fish skin collagen is not cross linked.

2. The composition according to claim 1, wherein the fish skin collagen is extracted from defatted fish skin dissolved in acids.

3. The composition according to claim 1, wherein the fish skin collagen is obtained by eliminating the telopeptide using pepsin.

4. The composition according to claim 1, wherein the squid chitin is laminated to fish skin collagen at 0°–20° C.

5. The composition according to claim 1, wherein the skin collagen is obtained from a cold fish selected from the group consisting of salmon, trout and walleye pollack.

* * * * *